(12) United States Patent
Borchert et al.

(10) Patent No.: US 6,194,610 B1
(45) Date of Patent: Feb. 27, 2001

(54) PROCESS FOR THE SELECTIVE PREPARATION OF ACETIC ACID USING A MOLYBDENUM AND PALLADIUM BASED CATALYTIC OXIDE

(75) Inventors: Holger Borchert, Bockenheim; Uwe Dingerdissen, Seeheim-Jungenheim, both of (DE)

(73) Assignee: Aventis Research & Technologies GmbH & Co. KG, Frankfurt am Main (DE)

( * ) Notice: Subject to any disclaimer, the term of this patent is extended or adjusted under 35 U.S.C. 154(b) by 0 days.

(21) Appl. No.: 09/230,553

(22) PCT Filed: Jul. 16, 1997

(86) PCT No.: PCT/EP97/03809

§ 371 Date: Jan. 28, 1999

§ 102(e) Date: Jan. 29, 1999

(87) PCT Pub. No.: WO98/05619

PCT Pub. Date: Feb. 12, 1998

(30) Foreign Application Priority Data

Jul. 31, 1996 (DE) ................................ 196 30 832

(51) Int. Cl.[7] ............................ C07C 51/16; B01J 21/16
(52) U.S. Cl. ...................... 562/548; 562/546; 562/547; 502/209; 502/210; 502/211; 502/212; 502/213; 502/214; 502/215; 502/248; 502/257; 502/305; 502/313
(58) Field of Search .................................. 562/548, 546, 562/547; 502/313, 305, 255, 257, 248, 215, 213, 212, 211, 210, 209

(56) References Cited

U.S. PATENT DOCUMENTS

| | | | |
|---|---|---|---|
| 3,970,697 | * | 7/1976 | Scheben et al. . |
| 3,976,688 | * | 8/1976 | Akiyama et al. . |
| 4,298,531 | | 11/1981 | Lindsey, Jr. et al. . |
| 4,499,301 | | 2/1985 | Murib . |
| 5,162,578 | * | 11/1992 | McCain, Jr. et al. . |
| 6,043,184 | * | 3/2000 | Karmakar et al. . |
| 6,060,419 | * | 5/2000 | Wijesekera . |
| 6,087,297 | * | 7/2000 | Karim et al. . |

FOREIGN PATENT DOCUMENTS

| | | |
|---|---|---|
| 0 113 156 A1 | 7/1984 | (EP) . |
| 0 608 838 A3 | 8/1994 | (EP) . |
| 0 620 205 A1 | 10/1994 | (EP) . |
| 2 040 717 | 9/1980 | (GB) . |

OTHER PUBLICATIONS

Patent Abstracts of Japan, vol. 95, No. 1, Feb. 28, 1995 & JP 06 293695 A, Oct. 21, 1994.

* cited by examiner

*Primary Examiner*—James O. Wilson
*Assistant Examiner*—Robert W. Deemie
(74) *Attorney, Agent, or Firm*—Frommer Lawrence & Haug LLP

(57) ABSTRACT

The present invention relates to a process for the selective preparation of acetic acid from a gaseous feed comprising ethane, ethylene or mixtures thereof plus oxygen at elevated temperature, which comprises bringing the gaseous feed into contact with a catalyst comprising the elements Mo, Pd, X and Y in gram atom ratios a:b:c:d in combination with oxygen $$Mo_a Pd_b X_c Y_d \qquad (I)$$

where the symbols X and Y have the following meanings:

X is one or more elements selected from the group consisting of: Cr, Mn, Nb, Ta, Ti, V, Te and/or W, in particular Nb, V and W;

Y is one or more elements selected from the group consisting of: B, Al, Ga, In, Pt, Zn, Cd, Bi, Ce, Co, Cu, Rh, Ir, Au, Ag, Fe, Ru, Os, K, Rb, Cs, Mg, Ca, Sr, Ba, Zr, Hf, Ni, P, Pb, Sb, Si, Sn, Tl and U, in particular Ca, Sb, Te and Li. The present invention further provides a catalyst for the selective preparation of acetic acid comprising the elements Mo, Pd, X and Y in the gram atom ratios a:b:c:d in combination with oxygen. The process can be illustrated by the following reaction scheme,

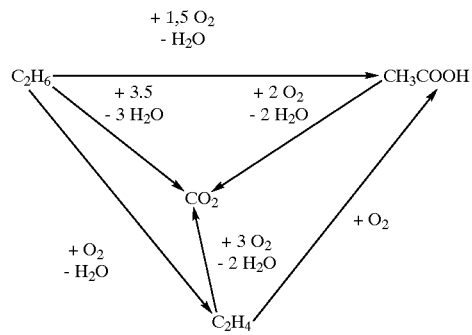

11 Claims, No Drawings

PROCESS FOR THE SELECTIVE PREPARATION OF ACETIC ACID USING A MOLYBDENUM AND PALLADIUM BASED CATALYTIC OXIDE

The present invention relates to a process for the selective preparation of acetic acid by catalytic gas-phase oxidation of ethane and/or ethylene in the presence of a palladium-containing catalyst.

The oxidative dehydrogenation of ethane to ethylene in the gas phase at temperatures of >500° C. is known, for example from U.S. Pat. No. 4,250,346, U.S. Pat. No. 4,524,236 and U.S. Pat. No. 4,568,790.

Thus, U.S. Pat. No. 4,250,346 describes the use of a catalyst composition comprising the elements molybdenum, X and Y in the ratio a:b:c for converting ethane into ethylene, where X is Cr, Mn, Nb, Ta, Ti, V, and/or W and Y is Bi, Ce, Co, Cu, Fe, K, Mg, Ni, P, Pb, Sb, Si, Sn, Tl and/or U and a is 1, b is from 0.05 to 1 and c is from 0 to 2. The total value of c for Co, Ni and/or Fe must here by less than 0.5.

The reaction is preferably carried out in the presence of added water. The disclosed catalysts can likewise be used for the oxidation of ethane to give acetic acid, with the efficiency of the conversion to acetic acid being about 18%, at an ethane conversion of 7.5%.

The abovementioned documents are concerned mainly with the preparation of ethylene, less with the target preparation of acetic acid.

In contrast, EP-B-0 294 845 describes a process for the selective preparation of acetic acid from ethane, ethylene or mixtures thereof using oxygen in the presence of a catalyst mixture comprising at least A.) a calcined catalyst of the formula $Mo_xV_y$ or $Mo_xV_yZ_y$, where Z is one or more of the metals Li, Na, Be, Mg, Ca, Sr, Ba, Zn, Cd, Hg, Sc, Y, La, Ce, Al, Tl, Ti, Zr, Hf, Pb, Nb, Ta, As, Sb, Bi, Cr, W, U, Te, Fe, Co and Ni, and x is from 0.5 to 0.9, y is from 0.1 to 0.4 and z is from 0.001 to 1, and B.) and ethylene hydration catalyst and/or ethylene oxidation catalyst. The second catalyst component B is, in particular, a molecular sieve catalyst or a palladium-containing oxidation catalyst. When the catalyst mixture described is used and a gas mixture comprising ethane, oxygen, nitrogen and water vapor is passed through the catalyst-containing reactor, the maximum selectivity is 27% at an ethane conversion of 7%. The high conversion rates of ethane are, according to EP 0 294 845, achieved only using the catalyst mixture described, but not using a single catalyst containing the components A and B.

A further process for preparing a product comprising ethylene and/or acetic acid is described in EP-B-0 407 091. Here, ethane and/or ethylene and a gas comprising molecular oxygen is brought into contact at elevated temperature with a catalyst composition comprising the elements A, X and Y. A is here $Mo_dRe_eW_f$, X is Cr, Mn, Nb, Ta, Ti, V and/or W and Y is Bi, Ce, Co, Cu, Fe, K, Mg, Ni, P, Pb, Sb, Si, Sn, Tl and/or U. The maximum selectivities which were able to be achieved when using the catalyst described in the oxidation of ethane to acetic acid are 78%. Further by-products formed are carbon dioxide, carbon monoxide and ethylene.

However, none of the publications listed above describes the use of a catalyst comprising the elements palladium and molybdenum for the selective oxidation of ethane and/or ethylene to give acetic acid. Furthermore, the selectivities achieved up to now in the prior art for the oxidation to acetic acid are still not satisfactory.

It is therefore an object of the invention to provide a process which allows ethane and/or ethylene to be oxidized in a simple and targeted manner and with high selectivity under very mild reaction conditions to give acetic acid.

It has now surprisingly been found that use of a catalyst comprising the elements molybdenum and palladium and one or more elements selected from the group consisting of chromium, manganese, niobium, tantalum, titanium, vanadium, tellurium and/or tungsten makes it possible to oxidize ethane and/or ethylene under relatively mild conditions, in a simple manner with high selectivity to give acetic acid. The present invention accordingly provides a process for the selective preparation of acetic acid from a gaseous feed comprising ethane, ethylene or mixtures thereof plus oxygen at elevated temperature, which comprises bringing the gaseous feed into contact with a catalyst comprising the elements Mo, Pd, X and Y in gram atom ratios a:b:c:d in combination with oxygen $$Mo_aPd_bX_cY_d \qquad (1)$$

where the symbols X and Y have the following meanings:
  X is one or more elements selected from the group consisting of: Cr, Mn, Nb, Ta, Ti, V, Te and/or W, in particular Nb, V and W;
  Y is one or more elements selected from the group consisting of: B, Al, Ga, In, Pt, Zn, Cd, Bi, Ce, Co, Cu, Rh, Ir, Au, Ag, Fe, Ru, Os, K, Rb, Cs, Mg, Ca, Sr, Ba, Zr, Hf, Ni, P, Pb, Sb, Si, Sn, Tl and U, in particular Ca, Sb and Li.

The indices a, b, c and d are the gram atom ratios of the corresponding elements, where
  a=1, b>0, c>0, and d=0–2.

If X and Y are a plurality of different elements, the indices c and d can likewise assume a plurality of different values.

The present invention further provides a catalyst for the selective preparation of acetic acid comprising the elements Mo, Pd, X and Y in the gram atom ratios a:b:c:d in combination with oxygen.

The gram atom ratios a:b:c:d are preferably within the following ranges:
  a=1;
  b=0.0001 to 0.5;
  c=0.1–1.0 and
  d=0–1.0.

Palladium contents in the catalyst which are above the upper limit specified promote the formation of carbon dioxide in the process of the invention. Furthermore, higher palladium contents are generally also avoided because they make the catalyst unnecessarily expensive. On the other hand, palladium contents below the limiting value specified favor ethylene formation.

The catalyst used according to the invention preferably comprises not only the elements molybdenum and palladium but also vanadium, niobium, antimony and calcium in combination with oxygen. The gram atom ratios $a:b:c^1:c^2:d^1:d^2$ of the elements Mo:Pd:V:Nb:Sb:Ca are preferably as follows:
  a(Mo)=1;
  b (Pd)=0.0001–0.5, in particular 0.0001–0.05;
  $c^1$(V)=0.1–1.0;
  $c^2$(Nb)=0.1–0.5;
  $d^1$(Sb)=0–0.5;
  $d^2$(Ca)=0–0.2.

Examples of such catalyst compositions which are preferably used in the process of the invention are:
  $Mo_{1.00}V_{0.25}Nb_{0.12}Pd_{0.0005}$ $Mo_{1.00}V_{0.25}Nb_{0.12}Pd_{0.0004}$
$Mo_{1.00}V_{0.25}Nb_{0.12}Pd_{0.0003}$
$Mo_{1.00}V_{0.36}Nb_{0.03}Sb_{0.01}Pd_{0.0005}$
$Mo_{1.00}V_{0.50}Nb_{0.15}Te_{0.2}Pd_{0.0002}$
$Mo_{1.00}V_{0.25}Nb_{0.3}W_{0.2}Pd_{0.0003}$
$Mo_{1.00}V_{0.25}Nb_{0.3}Sb_{0.1}Pd_{0.0004}$ The catalysts used according to the invention can be prepared by conventional methods. These start out from a slurry, in particular an aqueous solution, comprising the individual starting components of the elements in accordance with their proportions.

The starting materials for the individual components in the preparation of the catalyst of the invention are, apart from the oxides, preferably water-soluble substances such as ammonium salts, nitrates, sulfates, halides, hydroxides and salts of organic acids which can be converted into the corresponding oxides by heating. To mix the components, aqueous solutions or suspensions of the metal salts are prepared and mixed.

In the case of molybdenum, it is advisable to use the corresponding molybdates e.g. ammonium molybdate, as starting compounds because of their commercial availability.

Suitable palladium compounds are, for example, palladium(II) chloride, palladium(II) sulfate, tetramminepalladium(II) nitrate, palladium(II) nitrate and also palladium(II) acetylacetonate.

The reaction mixture obtained is then stirred at from 50 to 100° C. for from 5 minutes to 5 hours. The water is subsequently removed and the remaining catalyst is dried at a temperature of from 50 to 150° C., in particular from 80 to 120° C.

If the catalyst obtained is subsequently subjected to a calcination process, it is advisable to calcine the dried and pulverized catalyst at a temperature in the range from 100° C. to 800° C., in particular from 200 to 500° C., in the presence of nitrogen, oxygen or an oxygen-containing gas. The duration is from 2 to 24 hours.

The catalyst can be used without a support material or be mixed with an appropriate support material or applied thereto.

Suitable support materials are the customary materials such as porous silicon dioxide, ignited silicon dioxide, kieselguhr, silica gel, porous or nonporous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, aluminum silicate, silicon nitride or silicon carbide, but also meshes made of glass, carbon fibers, metal oxides or metals or corresponding monoliths.

Preferred support materials have a surface area of less than 100 m²/g. Preferred support materials are silicon dioxide and aluminum oxide having a low specific surface area. The catalyst can, after shaping, be used as a regularly or irregularly shaped support body or else in powder form as a heterogeneous oxidation catalyst.

The reaction can be carried out in a fluidized bed or in a fixed-bed reactor. For use in a fluidized bed, the catalyst is milled to a particle size in the range from 10 to 200 µm.

The gaseous feed comprises ethane and/or ethylene which are fed to the reactor as pure gases or in admixture with one or more other gases. Suitable additional or carrier gases of this type are, for example, nitrogen, methane, carbon monoxide, carbon dioxide, air and/or water vapor. The gas containing molecular oxygen can be air or a gas containing more or less molecular oxygen than air, e.g. oxygen. The proportion of water vapor can be in the range from 0 to 50% by volume. Higher water vapor concentrations would make the work-up of the resulting aqueous acetic acid unnecessarily more expensive for technical process reasons. The ratio of ethane/ethylene to oxygen is advantageously in the range between 1:1 and 10:1, preferably 2:1 and 8:1. Relatively high oxygen contents are preferred, since the achievable ethane conversion and thus the yield of acetic acid is higher. Preference is given to adding oxygen or the gas containing molecular oxygen in a concentration range outside the explosive limits under reaction conditions, since this simplifies the carrying out of the process. However, it is also possible to set the ethane/ethylene to oxygen ratio within the explosive limits.

The reaction is carried out at temperatures between 200 and 500° C., preferably from 200 to 400° C. The pressure can be atmospheric or superatmospheric, e.g. in the range between 1 and 50 bar, preferably from 1 to 30 bar.

The reaction can be carried out in a fixed-bed or fluidized-bed reactor. Advantageously, ethane is first mixed with the inert gases such as nitrogen or water vapor before oxygen or the gas containing molecular oxygen is fed in. The mixed gases are preferably preheated to the reaction temperature in a preheating zone before the gas mixture is brought into contact with the catalyst. Acetic acid is separated from the gas leaving the reactor by condensation. The remaining gases are recirculated to the reactor inlet where oxygen or the gas containing molecular oxygen plus ethane and/or ethylene are metered in.

Comparison of the catalysts of the invention with those known from the prior art shows that under identical reaction conditions (reaction input gas, pressure, residence time in the reactor) but at significantly lower temperatures the present catalysts even achieve higher acetic acid selectivities (Table 1; Ex. 3 (according to the invention): acetic acid selectivity=77%; Ex. 13 (EP-0 407 091): acetic acid selectivity=60%). In comparison with the catalyst composition described in U.S. Pat. No. 4,250,346, the selectivity of the reaction to acetic acid can be increased tremendously by means of the catalysts of the invention even under lower reaction pressures, temperatures and residence times (cf. Ex. 1 (according to the invention): T=250° C., p=7 bar, residence time=14 s, acetic acid selectivity=84%; Ex.12 (U.S. Pat. No. 4,250,346): T=280° C., p=15 bar, residence time=30 s, acetic acid selectivity=32%).

Likewise, the space-time yields can be greatly increased by means of the present catalysts (Table 1). Space-time yields represent the amount of acetic acid produced per unit time and unit catalyst volume. Higher space-time yields are desirable since this enables the size of the reactors and also the amount of circulated gas to be reduced.

When using the catalyst of the invention, the selectivity in the oxidation of ethane and/or ethylene to acetic acid is ≧60 mol %, preferably ≧75 mol %, in particular ≧80 mol %, at an ethane conversion of >4%, preferably >5%, in particular >6%, so that, in comparison with the prior art, the process of the invention enables an increase in the acetic acid yields to be achieved in a simple manner while simultaneously reducing the formation of undesired by-products.

EXAMPLES

The catalyst composition specified in the examples is given in relative atom ratios.
Catalyst Preparation
Catalyst (I)
A catalyst having the following composition was prepared
$Mo_{1.00}V_{0.25}Nb_{0.12}Pd_{0.0005}$
Solution 1

10.22 g of ammonium metavanadate in 250 ml of water.
Solution 2

61.75 g of ammonium molybdate and 0.039 g of palladium acetate in 200 ml of water.
Solution 3
27.51 g of niobium oxalate in 25 ml of water.

The solutions are stirred separately at 90° C. for 15 minutes. The third solution is then added to the first. The combined mixtures are stirred at 90° C. for 15 minutes before the second is added. The resulting mixture is stirred at 90° C. for 15 minutes. The water is subsequently removed on a hot plate until a thick paste is formed. This is dried at 120° C. overnight. The solid is crushed (sieve fraction: 0.35–2 mm) and subsequently calcined in static air at 400° C. for 4 hours. The catalyst is then sieved in order to obtain a sieve fraction between 0.35 and 1 mm.

Catalyst (II)

A catalyst having the following composition was prepared:

$Mo_{1.00}V_{0.25}Nb_{0.12}Pd_{0.0004}$

The preparation was carried out as described in Catalyst Example (I) except that 0.031 g instead of 0.039 g of palladium acetate was used.

Catalyst (III)

A catalyst having the following composition was prepared $Mo_{1.00}V_{0.36}Nb_{0.03}Sb_{0.01}Ca_{0.01}Pd_{0.0005}$ Solution 1
20.0 g of ammonium molybdate in 100 ml of water
Solution 2
4.8 g of ammonium metavanadate in 100 ml of water.
Solution 3
2.6 g of niobium oxalate, 0.48 g of antimony oxalate, 0.34 g of calcium nitrate in 50 ml of water.
Solution 4
0.013 g of palladium acetate in 50 ml of acetone.

The solutions 1 to 3 are stirred separately at 70° C. for 15 minutes. The third solution is then added to the second. The combined mixtures are stirred at 70° C. for 15 minutes before they are added to the first. Solution 4 is subsequently added thereto. The resulting mixture is stirred at 70° C. for 15 minutes. The water/acetone mixture is subsequently evaporated quickly until a thick paste is formed. This is dried at 120° C. overnight. The solid is crushed (sieve fraction: 0.35–2 mm) and subsequently calcined in static air at 300° C. for 5 hours. The catalyst is then sieved in order to obtain a sieve fraction between 0.35 and 0.7 mm.

Comparative Examples

Catalyst (IV)

For comparison, a catalyst corresponding to U.S. Pat. No. 4,250,346 having the following composition was prepared $Mo_{1.00}V_{0.25}Nb_{0.12}$ The preparation was carried out as described in Catalyst Example (I) except that no palladium acetate was used.

Catalyst (V)

For comparison, a catalyst corresponding to EP 0 407 091 having the following composition was prepared:

$Mo_{0.370}Re_{0.248}V_{0.259}Nb_{0.070}Sb_{0.030}Ca_{0.019}$

Solution 1
10.0 g of ammonium perrhenate and 9.7 g of ammonium molybdate in 50 ml of water.
Solution 2
4.5 g of ammonium metavanadate in 50 ml of water.
Solution 3
6.5 g of niobium oxalate, 1.34 g of antimony oxalate, 0.58 g of calcium nitrate in 180 ml of water.

These solutions are stirred separately at 70° C. for 15 minutes. The third solution is then added to the second. The combined mixtures are stirred at 70° C. for 15 minutes before they are added to the first. The resulting mixture is stirred at 70° C. for 15 minutes. The water is subsequently removed on a hot plate until a thick paste is formed. This is dried at 120° C. overnight. The solid is crushed (sieve fraction: 0.35–2 mm) and subsequently calcined in static air at 300° C. for 5 hours. The catalyst is then sieved in order to obtain a sieve fraction between 0.35 and 1 mm.

Method of Catalyst Testing

A steel reactor having an internal diameter of 10 mm was charged with 10 ml of the catalyst. The catalyst was heated to 250° C. under a stream of air. The pressure was subsequently set by means of an admission pressure regulator. The desired ethane:oxygen:nitrogen mixture was metered together with water into a vaporizer zone where water was vaporized and mixed with the gases. The reaction temperature was measured using a thermocouple in the catalyst bed. The reaction gas was analyzed on-line by gas chromatography.

In the examples, the following terms are defined as:

$$\text{ethane conversion } (\%) = 100 \times ([CO]/2 + [CO_2]/2 + [C_2H_4] + [CH_3COOH])/([CO]/2 + [CO_2]/2 + [C_2H_4] + [C_2H_6] + [CH_3COOH])$$

$$\text{Ethylene selectivity } (\%) = 100 \times ([C_2H_4])/([CO]/2 + [CO_2]/2 + [C_2H_4] + [CH_3COOH])$$

$$\text{Acetic acid selectivity } (\%) = 100 \times ([CH_3COOH])/([CO]/2 + [CO_2]/2 + [C_2H_4] + [CH_3COOH])$$

where

[ ]=concentrations in mol % and $[C_2H_6]$=concentration of the unreacted ethane.

The residence time is defined as:

$$\tau_-(S) = \text{bed volume of the catalyst (ml)/volume flow of the gas through the reactor based on the reaction conditions (ml/s).}$$

Reaction Procedure

The feed gas to the reactor consisted of 40% by volume of ethane, 8% by volume of oxygen, 32% by volume of nitrogen and 20% by volume of water vapor. The reaction conditions and results are summarized in the following table.

TABLE 1

| Ex. | Catalyst | Temperature (° C.) | Pressure (bar) | Residence time (s) | Ethane conversion (%) | Acetic acid selectivity (%) | Ethylene selectivity (%) | Space-time yield [kg/hm³] | CO + CO₂ selectivity (%) |
|---|---|---|---|---|---|---|---|---|---|
| 1 | (I) | 250 | 7 | 14 | 4 | 84 | 1 | 31 | 15 |
| 2 | (I) | 280 | 7 | 14 | 8 | 76 | 8 | 61 | 16 |
| 3 | (I) | 255 | 15 | 30 | 8 | 77 | 0 | 72 | 23 |
| 4 | (I | 245 | 15 | 30 | 6 | 82 | 0 | 53 | 18 |
| 5 | (I) | 280 | 15 | 30 | 10 | 77 | 2 | 72 | 21 |

TABLE 1-continued

| Ex. | Catalyst | Temperature (° C.) | Pressure (bar) | Residence time (s) | Ethane conversion (%) | Acetic acid selectivity (%) | Ethylene selectivity (%) | Space-time yield [kg/hm³] | CO + CO$_2$ selectivity (%) |
|---|---|---|---|---|---|---|---|---|---|
| 6 | (I) | 280 | 28 | 30 | 10 | 80 | 2 | 149 | 18 |
| 7 | (II) | 280 | 7 | 12 | 8 | 73 | 12 | 57 | 15 |
| 8 | (II) | 290 | 7 | 12 | 9 | 70 | 14 | 63 | 16 |
| 9 | (II) | 280 | 15 | 30 | 10 | 79 | 3 | 75 | 18 |
| 10 | (III) | 280 | 15 | 30 | 10 | 86 | 2 | 78 | 12 |
| 11 | (III) | 285 | 15 | 30 | 11 | 86 | 2 | 91 | 12 |
| 12 | (IV) | 280 | 15 | 30 | 9 | 32 | 57 | 28 | 11 |
| 13 | (V) | 280 | 7 | 14 | 4 | 39 | 55 | 4 | 6 |
| 14 | (V) | 280 | 15 | 30 | 4 | 61 | 29 | 28 | 10 |
| 15 | (V) | 300 | 15 | 30 | 9 | 60 | 29 | 28 | 11 |
| 16 | (V) | 300 | 28 | 60 | 9 | 79 | 12 | 92 | 9 |

Compared with the comparative catalysts (IV) and (V), the catalysts (I), (II) and (III) achieve significantly higher selectivities to acetic acid at lower temperatures and reaction pressures. Catalysts I ((Mo$_{1.0}$V$_{0.25}$Nb$_{0.12}$Pd$_{0.0005}$), II (Mo$_{1.0}$V$_{0.25}$Nb$_{0.12}$Pd$_{0.0004}$) and III (Mo$_{1.0}$V$_{0.36}$Nb$_{0.03}$Sb$_{0.01}$Ca$_{0.01}$Pd$_{0.0005}$)give higher space-time yields in comparison with the catalysts IV (Mo$_{1.0}$V$_{0.25}$Nb$_{0.12}$=U.S. Pat No. 4,250,346) and V (Mo$_{1.0}$Re$_{0.67}$V$_{0.70}$Nb$_{0.19}$Sb$_{0.08}$Ca$_{0.05}$=EP-0 407 091).

Comparative Experiments on the Thermal Stability of the Catalysts

In order to test the thermal stability of the catalysts, the catalysts (I) and (V) were installed in the reactor and operated for 100 hours (reaction conditions: 280° C., 15 bar, 30 seconds residence time, composition of the reaction gas: see above). After the operating time, a sample was taken in each case from the start of the catalyst bed and the composition was analyzed quantitatively. The compositions of the used and unused catalysts are compared in the following table.

TABLE 2

| Catalyst | Element | Composition before reaction (atom %) | Composition after reaction for 100 hours (atom %) |
|---|---|---|---|
| (V) | Mo | 38.0 | 44.0 |
| | Re | 23.9 | 13.3 |
| | V | 25.5 | 28.6 |
| | Nb | 7.0 | 8.0 |
| | Sb | 3.7 | 4.1 |
| | Ca | 1.7 | 2.0 |
| (I) | Mo | 72.7 | 72.6 |
| | V | 18.2 | 18.2 |
| | Nb | 8.7 | 8.9 |
| | Pd | 0.4 | 0.4 |

After only 100 hours of operation, catalyst (V) has lost 44.4% of the original rhenium. In contrast, the fresh and used catalyst (I) has the same composition.

What is claimed is:

1. An industrial large scale process for the selective preparation of acetic acid from a gaseous feed comprising ethane, ethylene or mixtures thereof plus oxygen at elevated temperature, which comprises bringing in a reactor the gaseous feed into contact with a catalyst comprising the elements Mo, Pd, X and Y in gram atom ratios a:b:c:d in combination with oxygen $$Mo_a Pd_b X_c Y_d \quad (I)$$

where the symbols X and Y have the meanings:

X is one or more elements selected from the group consisting of Cr, Mn, Nb, Ta, Ti, V, Te and W;

Y is one or more elements selected from the group consisting of B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Zr, Hf, Ni, P, Pb, Sb, Si, Sn, Tl and U;

the indices a, b, c and d are the gram atom ratios of the corresponding elements, where a=1; b>0; c>0; and d=0.05–2.

2. The process as claimed in claim 1, wherein X and/or Y are a plurality of elements, where, if desired, the indices c and d assume different values for different elements and wherein the sum of the gram atomic ratios of all elements of Y is 0–2.

3. The process as claimed in claim 1, wherein the temperature is in the range from 200 to 500° C.

4. The process as claimed in claim 1, wherein the pressure in the reactor is in the range from 1 to 50 bar.

5. The process as claimed in claim 1, wherein b is in the range from 0.0001 to 0.5.

6. The process as claimed in claim 1, wherein said gaseous feed comprises ethane mixed with at least one further gas.

7. The process as claimed in claim 6, wherein the further gas fed in is nitrogen, oxygen, methane, carbon monoxide, carbon dioxide, ethylene and/or water vapor.

8. The process as claimed in claim 1, wherein the catalyst comprises at least one of the following compositions in combination with oxygen:

Mo$_{1.00}$V$_{0.25}$Nb$_{0.12}$Pd$_{0.0005}$

Mo$_{1.00}$V$_{0.25}$Nb$_{0.12}$Pd$_{0.0004}$

Mo$_{1.00}$V$_{0.25}$Nb$_{0.12}$Pd$_{0.0003}$

Mo$_{1.00}$V$_{0.36}$Nb$_{0.03}$Sb$_{0.01}$Ca$_{0.01}$Pd$_{0.0005}$

Mo$_{1.00}$V$_{0.50}$Nb$_{0.15}$Te$_{0.2}$Pd$_{0.0002}$

Mo$_{1.00}$V$_{0.25}$Nb$_{0.3}$W$_{0.2}$Pd$_{0.0003}$

Mo$_{1.00}$V$_{0.25}$Nb$_{0.3}$Sb$_{0.1}$Pd$_{0.0004}$.

9. The process as claimed in claim 1, wherein the catalyst is mixed with a support material or is fixed on a support material.

10. The process as claimed in claim 1, wherein the selectivity of the oxidation reaction to acetic acid is ≧60%, at an ethane conversion of ≧4%.

11. A catalyst for the selective oxidation of ethane, ethylene or mixtures thereof plus oxygen, comprising the elements Mo, Pd, X and Y in gram atom ratios a:b:c:d in combination with oxygen $$Mo_aPd_bX_cY_d \qquad (I)$$

where the symbols X and Y have the meanings:

X is one or more elements selected from the group consisting of Cr, Mn, Nb, Ta, Ti, V, Te and W;

Y is one or more elements selected from the group consisting of B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Zr, Hf, Ni, P, Pb, Sb, Si, Sn, Tl and U;

the indices a, b, c and d are the gram atom ratios of the corresponding elements, where a=1; b>0; c>0; and d=0.05–2.

* * * * *